United States Patent [19]

Nieder et al.

[11] Patent Number: 5,030,238

[45] Date of Patent: Jul. 9, 1991

[54] HIP PROSTHESIS

[75] Inventors: Elmar Nieder, York; Arnold Keller, Kaihude, both of Fed. Rep. of Germany

[73] Assignees: GMT Gesellschaft für Medizinische Technik mbH; Waldemar Link GmbH & Co., both of Hamburg, Fed. Rep. of Germany

[21] Appl. No.: 174,257

[22] Filed: Mar. 28, 1988

[30] Foreign Application Priority Data

Mar. 27, 1987 [DE] Fed. Rep. of Germany ....... 3710233

[51] Int. Cl.⁵ ................................................ A61F 2/36
[52] U.S. Cl. ........................................ 623/23; 623/22
[58] Field of Search ....................... 623/16, 18, 22, 23, 623/13; 128/92 Z, 92 Y, 92 YP, 92 YQ, 92 YG, 92 YJ, 92 W

[56] References Cited

U.S. PATENT DOCUMENTS

| | | | |
|---|---|---|---|
| 3,466,670 | 9/1969 | Christiansen | 623/23 |
| 3,815,590 | 6/1974 | Deyerle | 623/23 X |
| 3,979,779 | 9/1976 | Zeibig et al. | 623/23 X |
| 4,106,128 | 8/1978 | Greenwald et al. | 623/22 X |
| 4,187,559 | 2/1980 | Greil et al. | 623/18 |
| 4,221,623 | 9/1980 | Heissler et al. | 623/23 X |
| 4,312,079 | 1/1982 | Dorre et al. | 623/23 |
| 4,394,370 | 7/1983 | Jefferies | 128/92 YQ X |
| 4,512,038 | 4/1985 | Alexander et al. | 623/16 X |
| 4,535,486 | 8/1985 | Roberts et al. | 623/22 |
| 4,546,501 | 10/1985 | Gustilo et al. | 623/23 |
| 4,645,507 | 2/1987 | Engelbrecht et al. | 623/23 |
| 4,658,808 | 4/1987 | Link | 623/16 |
| 4,764,171 | 8/1988 | Harder et al. | 623/23 X |

FOREIGN PATENT DOCUMENTS

| | | | |
|---|---|---|---|
| 0201407 | 11/1986 | European Pat. Off. | 623/23 |
| 3535158 | 4/1987 | Fed. Rep. of Germany | 623/22 |
| 8503426 | 8/1985 | World Int. Prop. O. | 623/16 |

Primary Examiner—Richard J. Apley
Assistant Examiner—D. F. Crosby
Attorney, Agent, or Firm—Peter K. Kontler

[57] ABSTRACT

A hip prosthesis wherein a saddle-shaped head has a seat flanked by two horns and engageable with the surface bounding a recess in the lower part of a damaged pelvic bone. The head is rotatably or rigidly secured to a substantially S-shaped adapter which, in turn, is rotatably or non-rotatably secured to the adjacent end of a shank that is implantable in the cavity of a femur. One or more distancing rings can be inserted between the adapter and the head.

88 Claims, 12 Drawing Sheets

HIP PROSTHESIS

BACKGROUND OF THE INVENTION

The invention relates to prostheses in general, and more particularly to improvements in hip prostheses of the type wherein a saddle-like head engages a pelvic bone and a shank is anchored in the cavity of the femur.

Prostheses of the above outlined type are popular and in widespread use, especially if the pelvic bone is damaged so that the acetabulum is useless and the head of the prosthesis must engage another portion of the hipbone. This can happen as a result of an accident or due to illness. As a rule, a substitute socket is formed in the lowermost portion of the remaining pelvis and the saddle-shaped head of the properly implanted prosthesis is maintained in sliding engagement with such substitute socket. The two horns of the saddle-shaped head of the prosthesis flank the substitute socket to prevent the head from leaving the socket. It is also possible to have the head of the prosthesis extend into a hole of the pelvis. Reference may be had to commonly owned U.S. Pat. No. 4,645,507 granted Feb. 24, 1987.

It has been found that heretofore known prostheses with saddle-like heads fail to satisfy all of the requirements which must be fulfilled by an artificial hip joint. First of all, when the wearer of the prosthesis is walking, relative movement between the head of the prosthesis and the socket of the pelvis entails a pronounced mechanical stressing of the remainder of the pelvis. When the pelvis and the femur perform large movements relative to each other, the horns of the saddle-like head of the implanted prosthesis strike the adjacent portions of the pelvis. Secondly, frictional engagement between the head of the implanted prosthesis and the adjacent portion of the pelvis brings about extensive wear upon the pelvis; in fact, the head is likely to penetrate into the pelvis and to shorten the respective lower extremity of the patient.

It was further discovered that, when the pelvis has undergone extensive damage (either as a result of an accident or as a result of illness), the muscles in the region of an implanted conventional prosthesis with a saddle-like head can exert only relatively small forces in a sense to straighten out the extremity into which the prosthesis is implanted because they are incapable of finding an appropriate lever arm for the application of conversion or transmission forces which are being generated thereby. Therefore, a patient wearing such a prosthesis is likely to limp because she or he must continuously strive to maintain the center of gravity of the body above the vertical axis which is common to the saddle-like head and the shank of the implanted artificial hip joint. Consequently, many patients prefer to forego or to prematurely interrupt therapies involving pronounced physical stresses which are necessary to save or prolong the life of a patient following a serious illness (such as the removal or partial removal of a malignant tumor) because the prospects of walking again, and especially of walking without a pronounced limp, are slim or nil.

OBJECTS AND SUMMARY OF THE INVENTION

An object of the invention is to provide a simple but versatile prosthesis which can be readily altered to suit the needs of a patient and which can be modified in the course of implantation.

Another object of the invention is to provide a hip prosthesis which can be used as a superior substitute for heretofore known hip prostheses.

A further object of the invention is to provide a novel and improved method of articulately connecting the parts of the above outlined prosthesis to each other.

An additional object of the invention is to provide novel and improved couplings and joints for use in the above outlined prosthesis.

Still another object of the invention is to provide a prosthesis which can be made shorter or longer in a simple and efficient way.

A further object of the invention is to provide a hip prosthesis which can be utilized regardless of the condition of the pelvic bone.

Another object of the invention is to provide a novel saddle-shaped head for use in the above outlined prosthesis.

A further object of the invention is to provide a novel and improved shank which can be used in the above outlined prosthesis as a means for anchoring the prosthesis in the femur.

An additional object of the invention is to provide the prosthesis with a novel and improved adapter which renders it possible to articulate the head and the shank relative to each other.

A further object of the invention is to provide a prosthesis which is designed in such a way that it takes into consideration the forces acting upon the head when the prosthesis is implanted.

Another object of the invention is to provide a prosthesis which can be made of a variety of different materials, which can damp shocks that develop when the patient is in motion, and which enables the patient to walk without limping or with a limp which is less pronounced than that of a patient wearing a conventional prosthesis.

The invention is embodied in an implantable hip prosthesis for use between a pelvic bone which has a recess at its underside and a femur which has an upper end with a downwardly extending cavity. The prosthesis comprises a substantially saddle-like head having two horns and a seat between the horns. The head is engageable with the pelvic bone so that the recess of the pelvic bone is adjacent the seat and is flanked by the horns of the head. The prosthesis further comprises a shank which is implantable into the cavity of the femur. The axis of the shank is laterally offset relative to the axis of the head. The axis of the head is substantially normal to the seat. The arrangement is preferably such that the axis of the head substantially coincides with the resultant of a first force which is applied by the weight resting on the head in implanted condition of the prosthesis and a second force which is applied to the head by the muscles of the patient. The second force can be said to be a force which exerts upon the head a pressure in addition to the weight resting on the head. The axis of the shank is or can be substantially vertical when the prosthesis is implanted and the patient is standing.

The improved prosthesis preferably further comprises an adapter which is interposed between the head and the shank. Such adapter can have a substantially S-shaped outline with a first end connected to the head and a second end connected to the shank. The S-shaped outline is also the outline of a central longitudinal plane of such adapter. The upper end face at the first end of the adapter can be inclined to the horizontal at an angle of up to 30 degrees in implanted condition of the prosthesis and in upright position of the patient wearing the prosthesis. The underside of the adapter (at the second end of its substantially S-shaped body) can also be inclined with reference to the horizontal. The underside can make with a horizontal plane an angle of up to 60 degrees, for example, approximately 30 degrees.

The head of the improved prosthesis can be provided with a wide convex surface which bounds the seat between the horns and engages the pelvic bone in the region of the recess when the prosthesis is properly implanted.

At least one distancing element can be disposed between the head and the adapter, and each distancing element can resemble or constitute a disc. Each disc can have a hole whose axis is substantially parallel to or coincides with the axis of the head. Such hole is desirable and often necessary if the prosthesis further comprises a coupling or joint between the adapter and the head. For example, the coupling can comprise a shaft, a stud, a pin or an analogous projection (hereinafter called shaft) which extends into a complementary or substantially complementary hole or socket (hereinafter called hole) in the underside of the head. The axis of the shaft can coincide with the axis of the head. The position of the shaft can be reversed, i.e., the shaft can be provided on the head and then extends into a hole which is provided in the top surface of the adapter. The hole for the shaft can be a blind hole. The coupling can define a pivot axis which is substantially parallel to or coincides with the axis of the head, i.e., the head and the adapter can turn relative to each other about such pivot axis. Alternatively, the coupling can comprise means for non-rotatably securing the shaft in the hole. At the very least, the securing means can be designed to offer at least some resistance to turning of the head relative to the adapter and/or vice versa. For example, the shaft can rotatably extend into a blind hole in the underside of the head and can be non-rotatably received in a registering bore or hole of the adapter. The means for non-rotatably securing the shaft in the hole of the adapter can include an externally threaded member (such as a grub screw) which is received in a tapped bore of the adapter and has a tip bearing against the adjacent portion of the shaft. The tapped bore in the adapter is or can be substantially horizontal when the prosthesis is implanted and the patient is standing. The shaft of the coupling or joint between the adapter and the head can constitute an integral portion of the adapter or of the head. Thus, if the shaft is rigid with the adapter, it can turn in a hole of the head and, if the shaft is rigid with the head, it can turn in a hole of the adapter. If desired, the shaft can be made rigid with the distancing element or elements between the adapter and the head, and such shaft can have a first end portion which is rotatably received in a hole of the adapter and a second end portion which is rotatably received in the head. The number of distancing elements between the head and the adapter will be selected by the surgeon according to the needs of a particular patient. The same or a similar result can be achieved by equipping the hospital wherein the implantations are performed with a supply of thin, medium thick or rather thick distancing elements so that the surgeon can select the distance between the head and the shank of the prosthesis by selecting the dimensions of the adapter and/or by selecting a single distancing element of appropriate thickness or a set of two or more superimposed distancing elements having a required combined thickness.

A friction reducing lining, e.g., a lining of suitable plastic material, can be interposed between the adapter and the head. Such lining can be provided in addition to or independently of a suitable bearing sleeve between the shaft of the aforementioned coupling and the head and/or adapter. For example, the friction reducing lining can include a washer between the neighboring surfaces of the head and the adapter, and the bearing sleeve can be received in the hole for one end portion of the shaft or in the holes for both end portions of the shaft if a median portion of the shaft is installed in one or more distancing elements.

A second coupling can be provided between the adapter and the shank. Such second coupling can include a shaft, pin, stub or trunnion (hereinafter called stub) which extends from the adapter to be received in a complementary bore, hole or socket (hereinafter called socket) of the shank, or vice versa. The stub can have a substantially conical shape and can taper in a direction from the shank toward the head (if the stub is rigid with the shank) or in the opposite direction if the stub is rigid with the adapter. The axis of the shank can coincide or nearly coincide with the axis of the stub of the second coupling. Means can be provided for non-rotatably holding the stub in its socket; at the very least, such holding means can be designed and mounted to offer at least some resistance to turning of the stub in its socket. It is also possible to design the second coupling in such a way that its stub constitutes or resembles a cylinder and extends into a complementary cylindrical socket. The axis of the shank can be offset with reference to the axis of such cylindrical stub.

It is further possible to provide means for non-rotatably securing the adapter to the head of the improved prosthesis, for example, if the pelvic bone of the patient is damaged to such an extent that it is advisable to avoid any movements between the head and the adapter. For the same reasons, it might be necessary or advisable to provide means for securing the head to the pelvic bone or to another bone of the patient. The securing means can be designed to affix the adapter to the pelvic bone, to affix the adapter to the head, to affix the adapter and the head to the pelvic bone or another bone, or to affix the head to the pelvic bone or another bone. The securing means can constitute a means for promoting the growth of bones in the region of the implanted prosthesis; such growth promoting means can include portions of bones. The prosthesis can employ strip- or band-shaped securing means which are affixed to the pelvic bone or to another bone on the one hand, and to the head and/or adapter on the other hand, by metallic pins or the like. The utilization of fragments or portions of bones in the region of the pelvic bone is often desirable and advantageous because such undertaking promotes a regeneration of the pelvic bone. The fragments or portions of bones can be implanted in immediate or close proximity to the pelvic bone so as to serve as a means for promoting regeneration of the pelvic bone and/or as a means for independent bone growth in the region of the pelvic bone.

The head can be immobilized relative to the adapter in many other ways. For example, the coupling between the head and the adapter can comprise an externally toothed shaft on the adapter or the head and a hole provided in the head or the adapter. The hole is bounded by teeth which are complementary to and mate with the external teeth of the shaft so that the shaft prevents the head and the adapter from turning relative to each other. A threaded fastener can be introduced axially through the just mentioned shaft to hold the shaft from movement axially and away from the hole. Alternatively, the surface of the head which confronts the respective end of the adapter can be provided with radially extending teeth mating with complementary teeth on the adjacent surface of the adapter to hold the head and the adapter against angular movement relative to each other.

The prosthesis can comprise a flange or collar, preferably a relatively large flange, which is disposed between the head and the shank, preferably on the adapter adjacent the shank, to overlie the femur when the shank is properly implanted. At least the major surface of the shank can be smooth. However, it is equally possible to roughen (e.g., serrate) at least a portion of the external surface of the shank in order to hold it against turning in the cavity of the femur. For example, the external surface of the shank can be provided with at least one longitudinally extending flute, and such flute can be bounded by one or two longitudinally extending sharp edges. The shank can be designed to be a tight fit in the cavity of the femur so that it can be implanted without the need for introduction of bone cement around the shank. Means can be provided for securing to the femur that end portion of the properly implanted shank which is remote from the adapter and from the head. Bone material can be introduced into the cavity of the femur to surround the shank, particularly that portion of the shank which is adjacent the adapter. Alternatively, or in addition to bone material, at least a portion of the cavity can be filled with bone cement. The shank can constitute a complete femoral prosthesis, i.e., it can replace a major portion of or even the entire femur. It is also possible to assemble the shank of a male section and a female section which receives the male section. The female section can be rigid with or can be separably and movably connected to the adapter or directly to the head. Alternatively, the male section can be integral with or separably secured to the adapter and then extends in a direction away from the head and into the female section. The female section can include a well known Reimers lock which can be integral with the aforementioned flange or collar. Means (such as a threaded fastener or a pin) can be provided to secure the male and female sections of the composite shank to each other.

The head of the prosthesis can be made of a metallic material (such as titanium), of a suitable plastic material or of a suitable ceramic material. A friction reducing layer can be provided at least on that portion of the head which bounds the seat. Such layer can consist of or can contain a ceramic material and can resemble a saddle.

The adapter can also be made of a metallic material (such as titanium), of a suitable plastic material or of a suitable ceramic material. The aforementioned lining which is preferably provided in the hole for the shaft of the coupling between the adapter and the head can comprise or consist of a suitable plastic material, e.g., polyethylene. The lining can serve to reduce friction between the head and the adapter if the head and the adapter are turnable relative to each other. The shaft of the coupling between the adapter and the head can extend into an open-ended hole of the adapter so that one end of the shaft can be reached by a suitable tool by way of one open end of the hole in the adapter. For example, the tool can be used to move the shaft to a requisite axial position in which a notch in the peripheral surface of the shaft can receive the tip of the aforementioned screw serving as a means for releasably holding the shaft in the hole of the adapter. As mentioned above, the screw can be received in a substantially horizontal tapped bore or hole of the adapter.

The axis of the head can extend at right angles to a plane which is tangential to the lowermost or deepmost point of the surface bounding the seat between the horns of the head.

That portion of the adapter between the head and the shank of the improved prosthesis which is adjacent the axis of the head and the axis of the shaft forming part of the coupling between the head and the adapter is preferably configurated in a specific way to render the prosthesis more convenient to and more readily implantable into the hip joint of a particular patient. For example, the adapter can be made of steel and its length (between the surfaces facing the head and the shank) can be selected with a view to render the prosthesis most suited for implantation into the hip joint of a particular patient. The same holds true for the curvature of a substantially S-shaped adapter and the spacing of several portions of the adapter from the axis of the shaft forming part of the coupling between the adapter and the head. The axis of the shaft can coincide with the axis of the head, i.e., with the resultant of the aforediscussed force generated by the weight resting on the head and additional forces, such as those exerted by the muscles of the patient. Otherwise stated, the axis of the shaft can be parallel with or can coincide with the neutral layer of the adapter. The neutral layer is that zone of the adapter wherein the forces acting upon the adapter neutralize each other. The axis of such shaft can make with the vertical an angle of up to 30 degrees when the person wearing the prosthesis is standing. One of the presently preferred angles is in the region of 16 degrees.

The joint or coupling between the head and the adapter can constitute or resemble a universal joint. Such universal joint can include a spherical portion on the head or on the adapter and a suitable socket for the spherical portion in the adapter or in the head. The socket can be a substantially pan-shaped part, and the external surface of the complementary male portion then departs from a truly spherical surface. It is also possible to connect the head and the adapter to each other by a joint or coupling having a slide provided on the adapter or on the head and extending into a track which is defined by a complementary rail on the head or on the adapter.

Damper means can be interposed between the adapter and the head of the improved prosthesis.

If the adapter is a substantially S-shaped member, it can include a substantially straight portion having a predetermined length and a predetermined inclination to the horizontal in upright position of the patient wearing the prosthesis, and the ratio of the length to inclination of the elongated adapter portion is preferably constant.

The novel features which are considered as characteristic of the invention are set forth in particular in the appended claims. The improved prosthesis itself, however, both as to its construction and the mode of implanting the same, together with additional features and advantages thereof, will be best understood upon perusal of the following detailed description of certain specific embodiments with reference to the accompanying drawing.

BRIEF DESCRIPTION OF THE DRAWING

FIG. 22 is similar to FIG. 2 but shows the coupling between the adapter and the shank reversed; and FIG. 23 is a partly sectional elevational view of another hip prosthesis in which the shank constitutes a total femoral prosthesis.

DESCRIPTION OF THE PREFERRED EMBODIMENTS

Figures 1, 2:
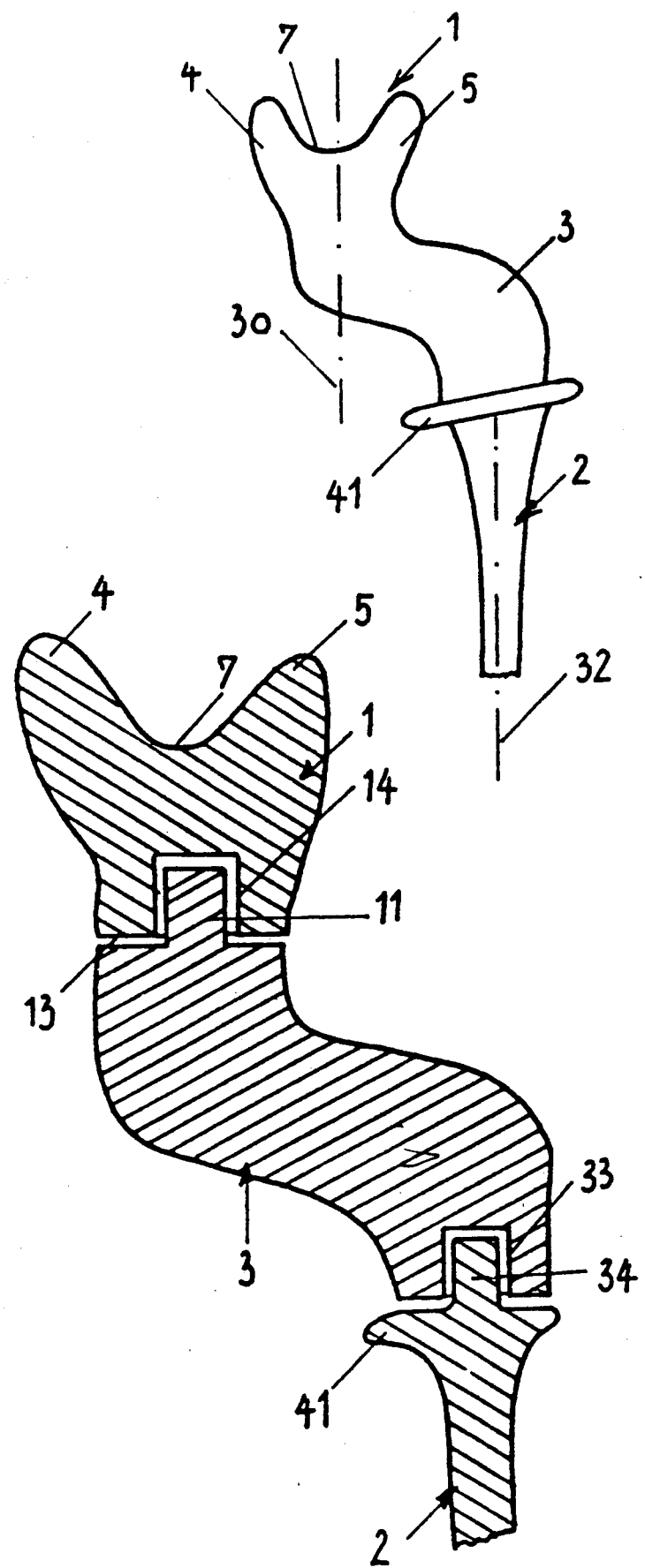
FIG. 1 is an elevational view of a hip prosthesis which embodies one form of the invention.
FIG. 2 is a central vertical sectional view of a prosthesis with couplings between the head and the adapter on the one hand, and the adapter and the shank on the other hand, a portion of the shank being broken away.
Figure 4:
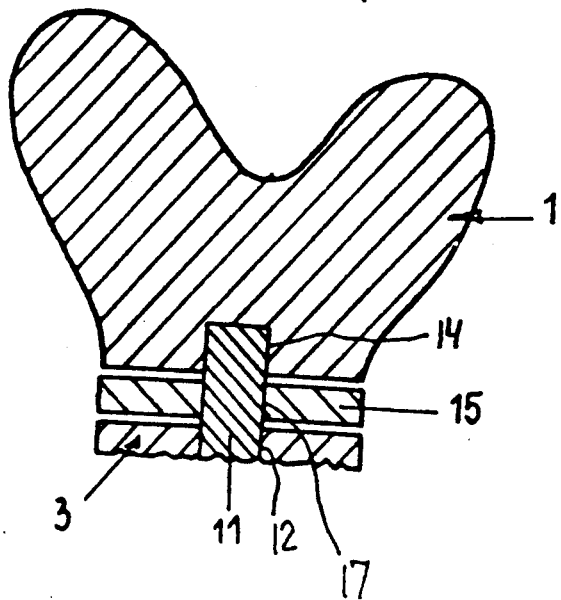
FIG. 4 is a fragmentary sectional view of a prosthesis with a single disc-shaped distancing element between the adapter and the head.
Figure 11:
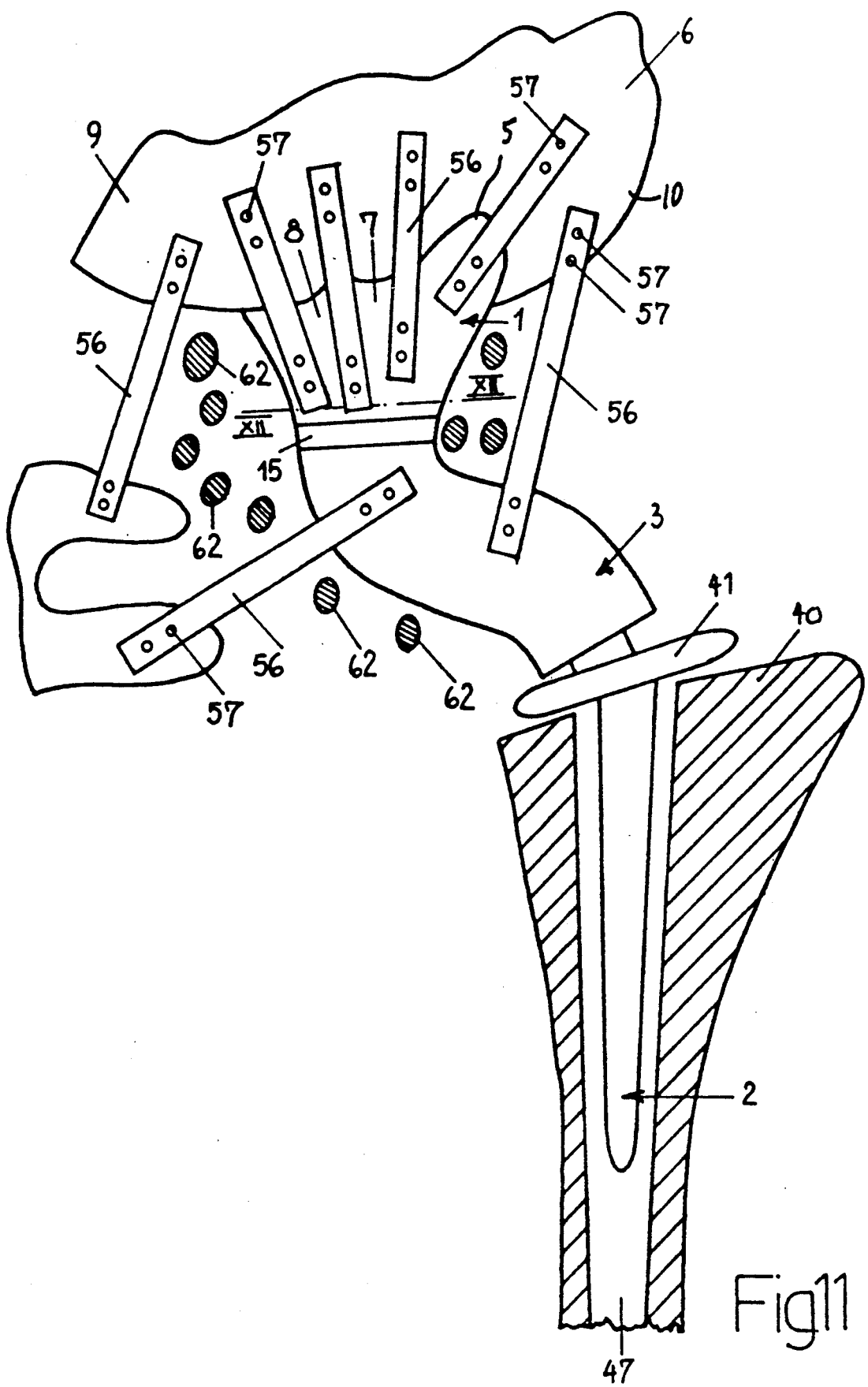
FIG. 11 is an elevational view of a further hip prosthesis wherein the head and the adapter are fixedly secured to the neighboring bones.

The hip prosthesis which is shown in FIG. 1 comprises a saddle-like head 1 with a seat 7 between two horns 4, 5, an intermediate portion 3 (hereinafter called adapter for short), and a shank 2 which is provided with a relatively large flange or collar 41 serving to overlie the upper end of a femur 40 (FIG. 11) having a cavity 47 in which the shank 2 is received when the prosthesis is implanted into the hip of a patient. FIG. 11 further shows a portion of a pelvic bone 6 having at its underside a recess 8 adjacent the seat 7 and flanked by the horns 4, 5 of the head 1. The head 1 can also extend into a hole (not specifically shown) in the pelvic bone. Reference may be had to FIG. 4 of commonly owned U.S. Pat. No. 4,645,507 granted Feb. 24, 1987 to Eckart Engelbrecht et al. for "Prosthesis". As shown in FIG. 11, at least a portion of the horn 5 is located in front of a bone portion 10 which is disposed at one side of the recess 8, and at least a portion of the other horn 4 (not visible in FIG. 11) is located behind a bone portion 9 at the other side of the recess 8 at the underside of the pelvic bone 6. Such implantation of the head 1 ensures that the head provides a proper vertical guidance for the upper part of the respective lower extremity.

As can be seen in FIG. 2, the head 1 can be made to turn relative to the adapter 3 because these parts of the prosthesis are or can be turnably connected to each other by a coupling including a shaft 11 (e.g., a short cylinder which is integral with the adapter) which extends into a complementary hole 14 in the lowermost portion 13 of the head 1. An analogous coupling is provided between the shank 2 and the adapter 3; it comprises a stub 34 which is rigid or integral with the flange 41 of the shank 2 and is received in a complementary socket 33 of the adapter 3. The axis of the shaft 11 is or can be substantially vertical when the patient wearing the prosthesis is standing, and such axis can coincide with the axis 30 of the head 1. The axis 30 is parallel or nearly parallel with and is laterally offset from the axis 32 of the shank 2. The axis 32 can coincide with the axis of the stub 34.

Figure 8:
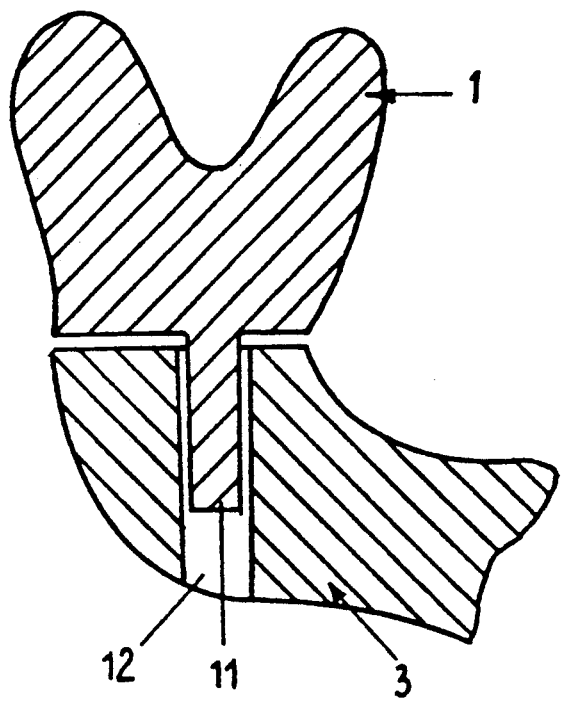
FIG. 8 is a fragmentary sectional view of a further hip prosthesis wherein the shaft of the coupling between the head and the adapter is integral with the head.

The shaft 11 can form an integral part of the head 1 (see FIG. 8) and then extends into a complementary hole 12 of the adapter 3. Analogously, the stub 34 can form an integral part of the adapter 3 and then extends into a complementary socket 33 of the flange or collar 41 as illustrated in FIG. 22.

Figure 7:
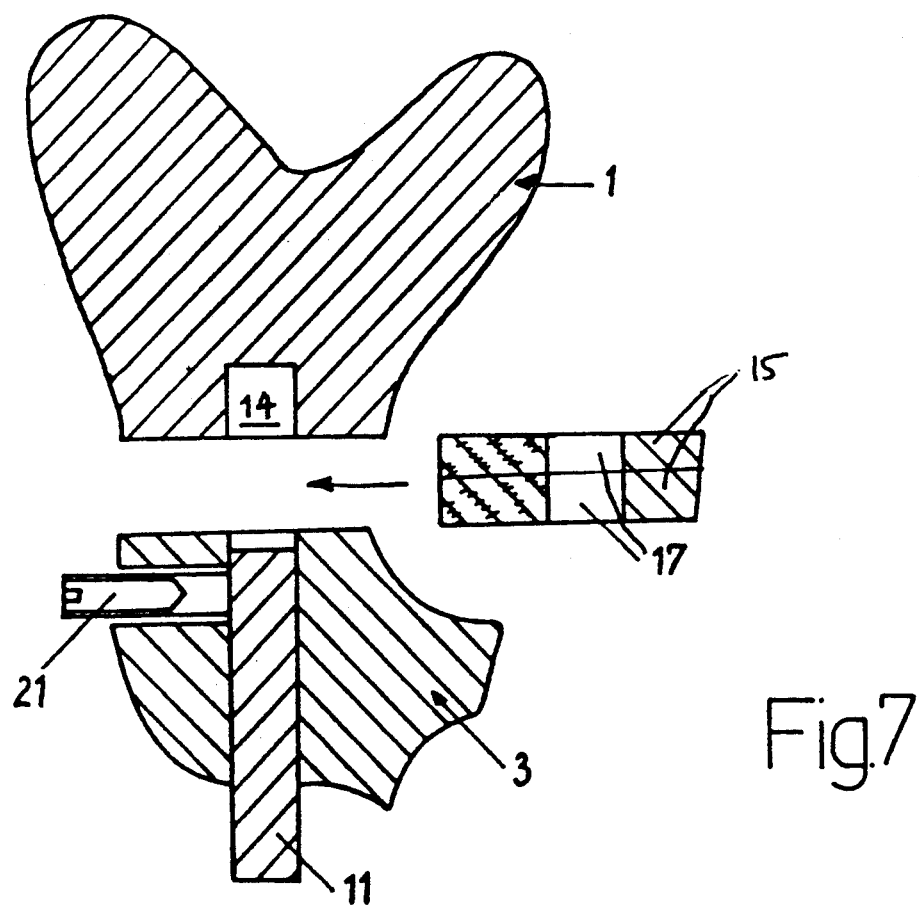
FIG. 7 illustrates one mode of installing a pair of superimposed distancing elements between the head and the adapter of the hip prosthesis.

FIG. 4 shows that at least one substantially washer- or disc-shaped distancing element 15 can be installed between the head 1 and the adapter 3 if the combined length of the parts 1, 3 is not sufficient for implantation in the hip of a particular patient. FIG. 7 shows that the prosthesis can be implanted with a plurality of distancing elements 15 (e.g., two registering distancing elements) between the head 1 and the adapter 3. The shaft 11 extends through a central opening or hole 17 of the distancing element 15 which is shown in FIG. 4. If desired or practical, the shaft 11 can be non-movably installed in the opening 17 of the distancing element 15 and then rotatably extends into the hole 14 of the head 1 and/or into the hole 12 of the adapter 3.

Figure 15:
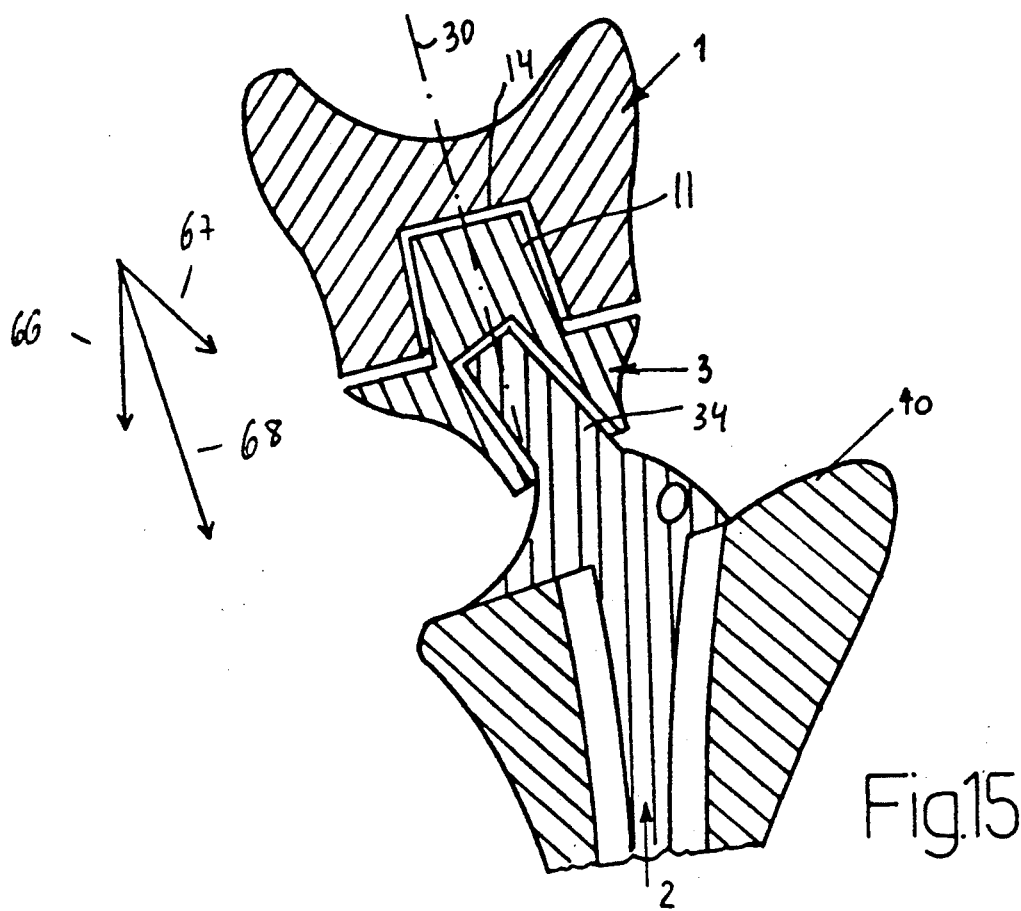
FIG. 15 is a sectional view of a further prosthesis with a modified adapter and a modified coupling between the adapter and the shank, further showing a force diagram wherein the resultant indicates the preferred inclination of the axis of the head.

Referring to FIG. 15, there is shown a diagram wherein the arrow 68 denotes a force which is the resultant of a vertical or nearly vertical first force 66 representing the weight which is borne by the head 1 of an implanted prosthesis when the patient is standing, and a second force 67 representing the forces applied to the adapter 3 by the muscle or muscles next to it. The direction of action of the resultant force 68 coincides with the axis 30 of the head 1; such axis can be normal to a plane which is tangential to the lowermost point of the saddle-like surface bounding the seat 7 between the horns 4 and 5 of the head 1. The just described orientation of the axis 32 can be achieved by appropriate selection of the dimensions and/or configuration of the adapter 3. The aforementioned muscle is connected to the pelvic bone 6 and to the femur 40.

Figure 3:
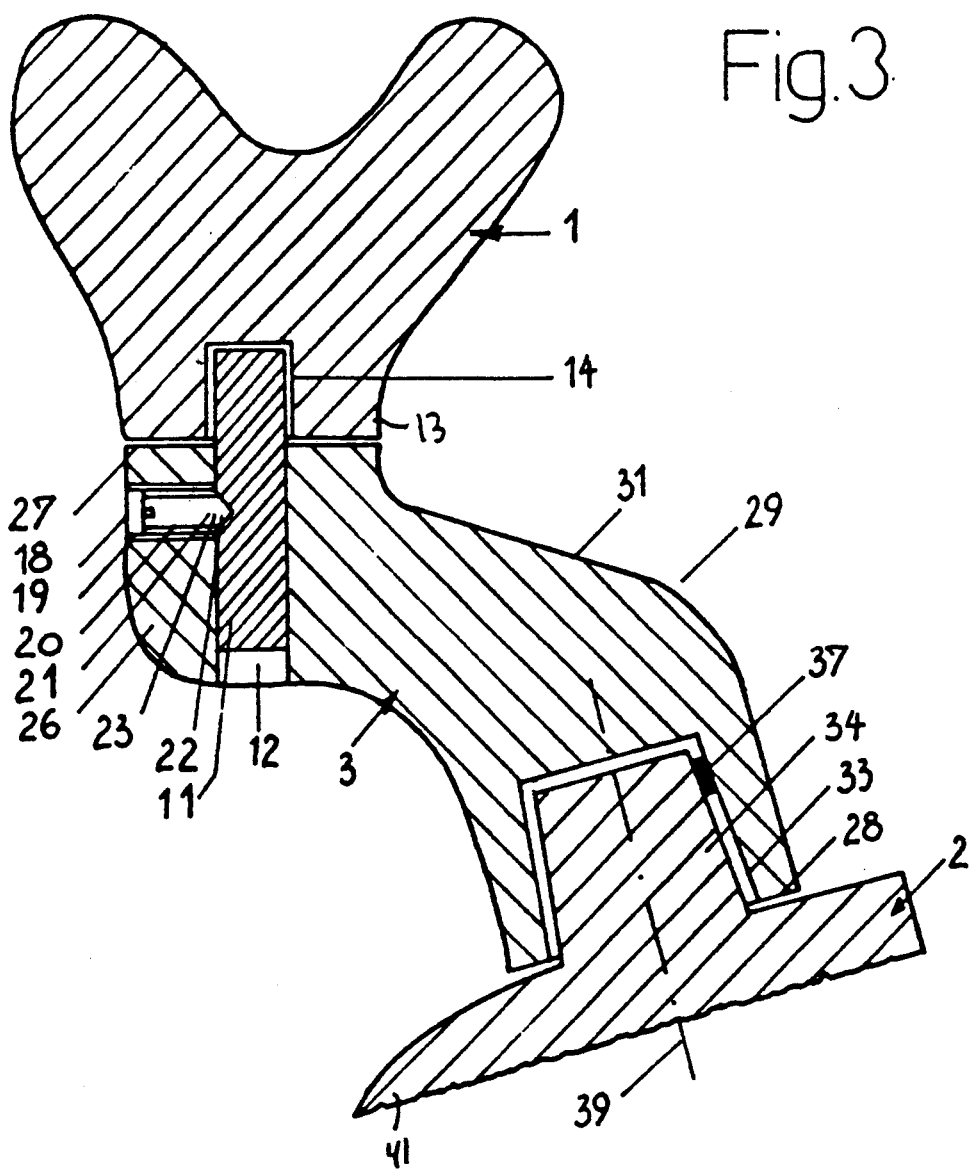
FIG. 3 is a similar sectional view of a prosthesis with a modified coupling between the head and the adapter.

FIG. 3 shows that the shaft 11 can constitute a separate component having a first portion extending into the blind hole 14 in the underside of the head 1 and a second portion received in a through hole 12 extending downwardly from the upper end face or surface 27 of the adapter 3. The means for non-rotatably securing the lower portion of the shaft 11 in the hole 12 of the adapter 3 comprises a threaded fastener 21 in a tapped horizontal bore or hole 18 of the adapter 3. The conical tip 22 of the fastener 21 (such as a grub screw) extends into a complementary notch 23 in the peripheral surface of the lower portion of the shaft 11. The internal thread in the bore or hole 18 is shown at 19, and the external thread of the screw 21 is shown at 20. The tip 22 cooperates with the surface bounding the notch 23 to hold the shaft 11 against axial movement in the hole 12 of the adapter 3.

Figure 9:
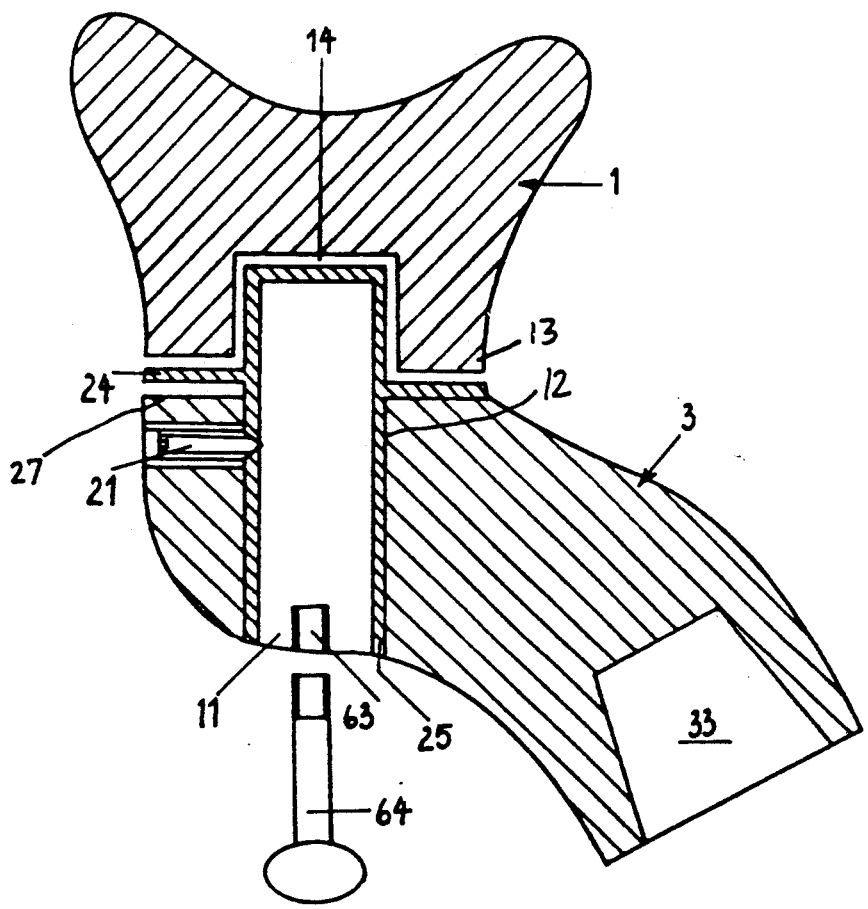
FIG. 9 is a fragmentary sectional view of an additional hip prosthesis wherein the holes in the head and adapter for the shaft of the coupling between such parts are lined with plastic material, and further showing a tool which can be used to select the axial position of the shaft.

FIG. 9 shows that the hole 14 in the head 1 and the hole 12 in the adapter 3 can be surrounded by a combined lining 24 and bearing sleeve 25 made of a preferably plastic material which is softer than the material of the head 1. For example, the parts 24, 25 can be made of polyethylene. The parts 24, 25 can reduce friction between the head 1 and the adapter 3 and/or take up at least some shocks when the prosthesis is implanted in the hip of a patient. Polyethylene constitutes but one of numerous plastic and/or other materials which can be used to make the lining 24 and/or the bearing sleeve 25. The lining 24 is disposed between the lowermost portion 13 of the head 1 and the adjacent end face 27 of the adapter 3. The lining 24 may but need not be integral with the sleeve 25; the illustrated design is preferred because it simplifies insertion of the parts 24, 25 between the head 1 and the adapter 3 and into the respective holes 14, 12.

Referring again to FIG. 3, the section through the adapter 3 is taken in a vertical plane 26 which has a substantially S-shaped outline. The upper end face 27 is substantially parallel to the underside of the lowermost portion 13 of the head 1 and is horizontal or nearly horizontal when the prosthesis of FIG. 3 is implanted and the patient is standing. However, it is equally within the purview of the invention to select the upper end face 27 in such a way that it is inclined to the horizontal.

The bottom surface 28 of the adapter 3 of FIG. 3 is inclined to the horizontal at an acute angle of up to 30 degrees. This angle can be smaller or even much larger than 30 degrees, e.g., up to 70 degrees.

The plane 26 of the adapter 3 is bounded in part by a line 29 having an uppermost portion which is substantially parallel to the axis 30 of the head 1 and then slopes downwardly, as at 31, e.g., at an angle of approximately 16 degrees. This angle can be anywhere between 10 and 30 degrees. The lowermost portion of the boundary line 29 is parallel or nearly parallel to the axis 32 of the shank 2 and/or to the axis 39 of the stub 34 and terminates at the underside 28 of the adapter 3.

Figure 5:
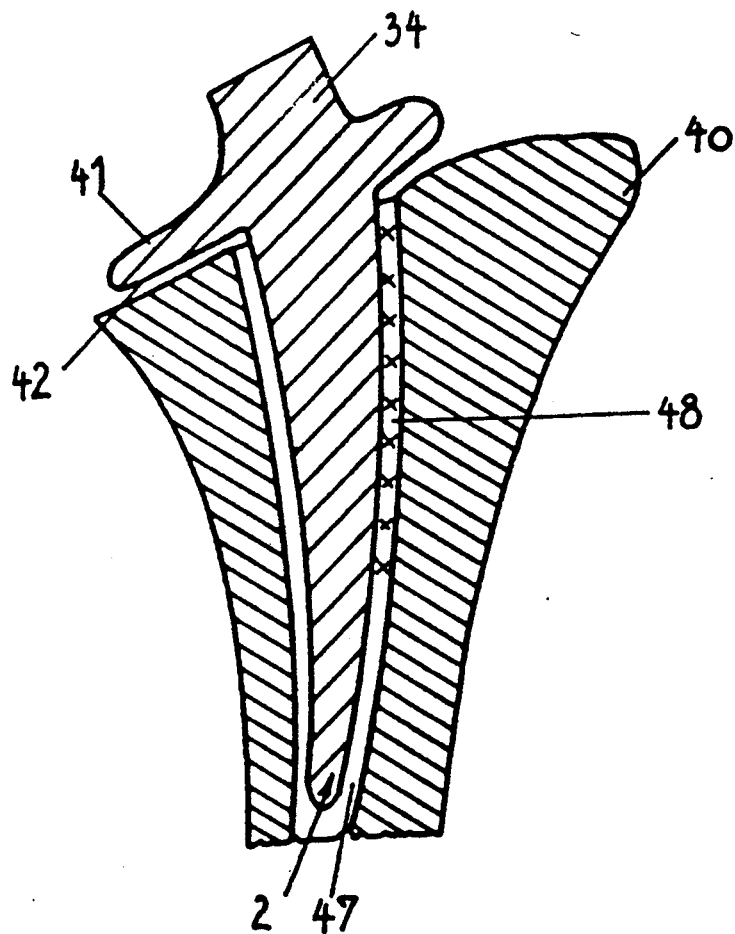
FIG. 5 shows one mode of implanting a substantially wedge-like shank in the cavity of the femur.
Figure 16:
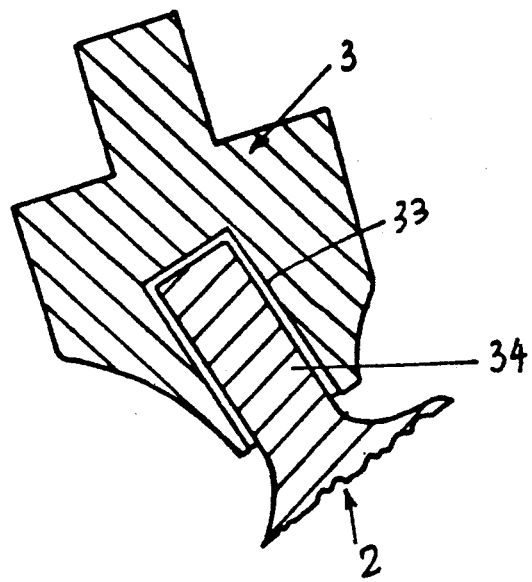
FIG. 16 is a fragmentary sectional view of an additional prosthesis wherein the coupling between the adapter and the shank comprises a cylindrical stub.

The socket 33 in the bottom surface 28 of the adapter 3 which is shown in FIG. 3 receives an insert 37 constituting a means for opposing or preventing any turning of the adapter 3 and shank 2 relative to each other. The insert 37 can be said to constitute a brake which is in requisite frictional engagement with the surface bounding the stub 34 and/or with the surface bounding the socket 33. The stub 34 of FIG. 3 is a relatively short conical frustum; however, and as shown in FIG. 16, it is also possible to employ a substantially cylindrical stub 34 which is received in a complementary cylindrical hole or socket 33 of the adapter 3. The stub 34 of FIG. 3 tapers in a direction toward the head 1, i.e., away from the flange or collar 41 of the shank 2. The stub 34 tapers in the opposite direction if it is an integral or separable part of the lower portion of the adapter 3. FIG. 5 shows that the underside 42 of the flange 41 can rest directly on the upper end portion of the femur 40 at the inlet end of the cavity 47 for the shank 2. The inclination of the underside 42 of the flange 41 to a horizontal plane can be in the range of 0–70 degrees. A presently preferred inclination is approximately 30 degrees.

Figure 6:
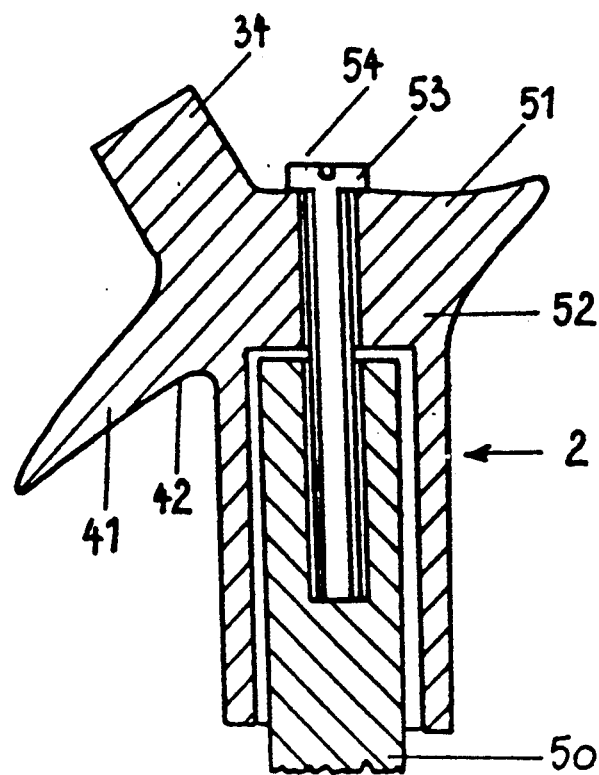
FIG. 6 is a fragmentary sectional view of an adapter and of a modified shank which has male and female sections secured to each other by a threaded fastener.

In the embodiment of FIG. 5, the flange 41 is an integral part of the shank 2 and is also integral with the stub 34. The shank 2 resembles an arcuate wedge and is surrounded by a layer of bone cement 48 which fills the cavity 47 around the shank. However, and as shown in FIG. 6, the flange 41 can constitute a separately produced part which is thereupon joined to the major part of the shank 2, namely to that part of the shank which is actually received in the cavity 47 of the femur 40. If the flange 41 is produced as a separate part, it can be provided with a threaded portion which extends into a complementary tapped bore or hole of the shank 2, or vice versa.

The bone cement 48 can be omitted if the shank 2 is designed to fit snugly into cavity 47 of the femur 40. The shank 2 can be substantially straight (FIG. 1) or it can have an arcuate shape (FIG. 5). Furthermore, as illustrated in FIG. 23 the shank 2 can constitute a total femoral prosthesis which extends through the diaphysis in a direction toward the epiphysis.

Figure 10:
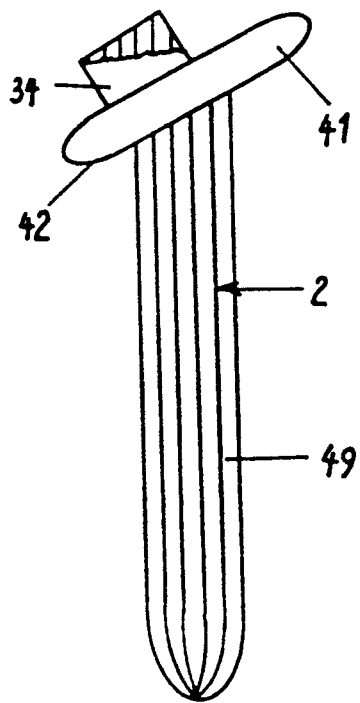
FIG. 10 is an elevational view of a shank whose external surface is provided with longitudinally extending flutes.

At least the major part of the external surface of the shank 2 can be smooth. However, and as shown in FIG. 10, the external surface of the shank 2 can be provided with one or more longitudinally extending flutes 49 which are bounded by sharp longitudinally extending edges, i.e., the flutes 49 can alternate with longitudinally extending teeth which reduce the likelihood of turning of the shank 2 in the cavity 47 of the femur 40.

FIG. 6 shows that the shank 2 can comprise a male section 50 which is entirely embedded in the femur 40 when the prosthesis is properly implanted, and a female section 51 which is secured to the male section 50 by a threaded fastener 53 extending through the flange 41 and into the adjacent end portion of the male section 50. The head 54 of the fastener 53 abuts the adjacent upwardly oriented surface of the flange 41 adjacent the stub 34 of the coupling between the shank 2 and the adapter 3 (not shown in FIG. 6). The female section 51 of the shank 2 of FIG. 6 constitutes or includes a so-called Reimers lock 52. The male section 50 can constitute an elongated cylinder having a substantially constant diameter. Alternatively, the male section 50 can include a larger-diameter portion adjacent the flange 41 and a smaller-diameter portion which extends into the cavity 47 of the femur 40. The transition between the two portions of the male section can be gradual or stepwise.

Figure 12:
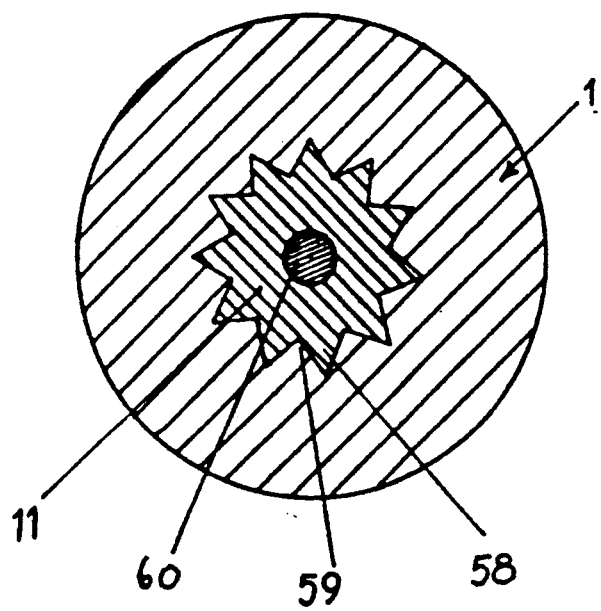
FIG. 12 is a horizontal sectional view of a modified head which non-rotatably receives the shaft of the coupling between the head and the adapter, the section being taken along the line XII—XII in FIG. 11.

FIG. 11 shows that the head 1 of the prosthesis can be fixedly secured to the pelvic bone 6 by a plurality of strip- or band-shaped securing means 56 whose end portions are affixed to the bone 6 and to the head 1 by metallic pins 57, screws or the like. Two of the securing means 56 shown in FIG. 11 serve to secure the adapter 3 directly to the pelvic bone 6 so as to avoid any turning of the adapter relative to the head 1. Such securing means will be resorted to when the pelvic bone 6 has undergone extensive damage as a result of an accident or due to an illness so that the surgeon wishes to prevent any, or any extensive, movements of the head 1 relative to the pelvic bone. The arrangement is preferably such that the adapter 3 and the head 1 cannot turn relative to each other. This can be achieved in a manner as shown in FIG. 12. Thus, the shaft 11 is integral with or is rigidly (non-rotatably) embedded in the adapter 3 and has external teeth 58 mating with internal teeth in the hole 59 of the head 1. A threaded fastener 60 is provided to affix the head 1 to the adapter 3 so that these parts cannot move axially of the shaft 11 and away from each other.

Figure 13:
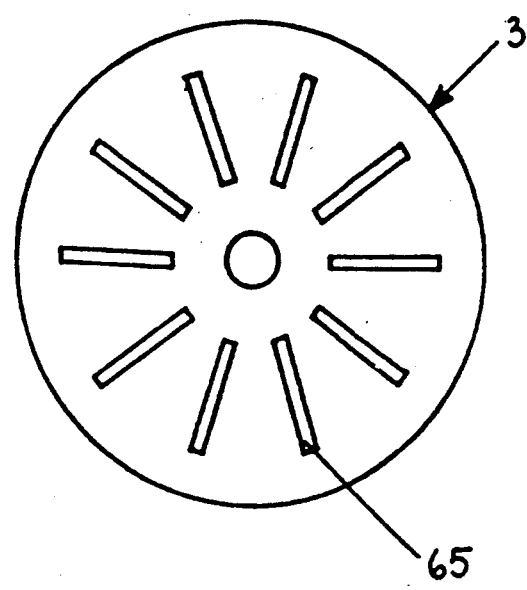
FIG. 13 is a plan view of a modified adapter having means for holding it against rotation relative to the head.
Figure 14:
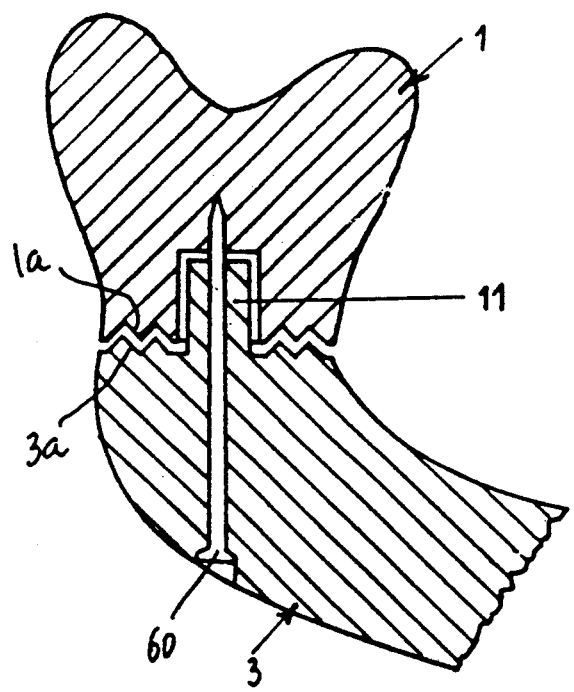
FIG. 14 is a fragmentary sectional view of a further prosthesis wherein the adapter and the head are held against rotation relative to each other in a different way.

Instead on relying of the externally toothed shaft 11 of FIG. 12, it is possible to prevent rotation of the adapter 3 and head 1 relative to each other in a manner as shown in FIG. 13 wherein the upper end face of the adapter is formed with radially extending teeth 65 which are receivable in complementary tooth spaces in the lowermost portion 13 of the head 1 (not shown in FIG. 13). Alternatively, and as shown in FIG. 14, it is possible to provide the upper end of the adapter 3 with a toothed surface 3a which is complementary to a toothed surface 1a at the underside of the head 1. A nail or a threaded fastener 60 is provided to extend through the shaft 11 and into the material of the head 1 in order to hold the surfaces 1a, 3a against movement away from each other. At least some of the teeth on the surfaces 1a, 3a are distributed and configured in such a way that they prevent the adapter 3 from turning about the axis of the shaft 11 relative to the head 1 and/or vice versa.

Referring again to FIG. 11, the securing means 56 are adjacent to means 62 for promoting bone growth in the region of the pelvic bone 6. The means 62 can constitute implanted bone fragments which can promote the growth of the pelvic bone 6.

The shank 2, the head 1 and the adapter 3 can be made of a metallic material, such as titanium. However, it is equally possible to make at least a portion of the component 1, 2 and/or 3 of the improved prosthesis from a suitable plastic or ceramic material.

Figure 17:
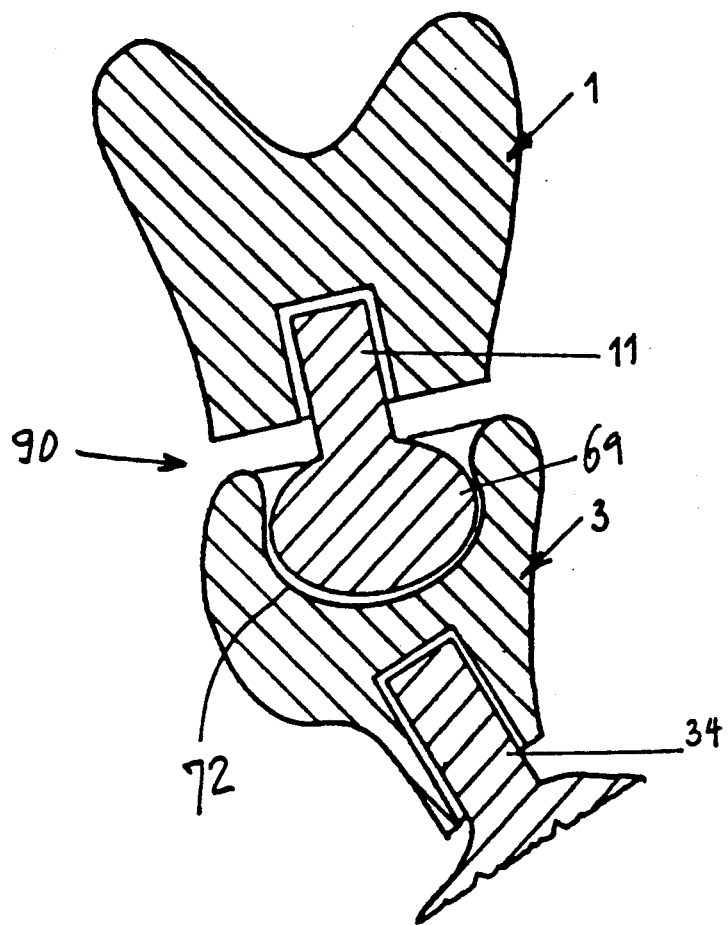
FIG. 17 is a fragmentary sectional view of a prosthesis wherein the coupling between the adapter and the head includes a universal joint.

In order to reduce the likelihood of the application of excessive stresses to the pelvic bone 6 in the region of the recess 8 (or the aforementioned opening), the head 1 and the adapter 3 can be coupled to each other by a universal joint. Reference may be had to FIG. 17 which shows a universal joint 90 with a substantially spherical male coupling member or portion 69 at the lower end of the shaft 11 and a complementary socket 72 in the upper portion of the adapter 3.

Figure 18:
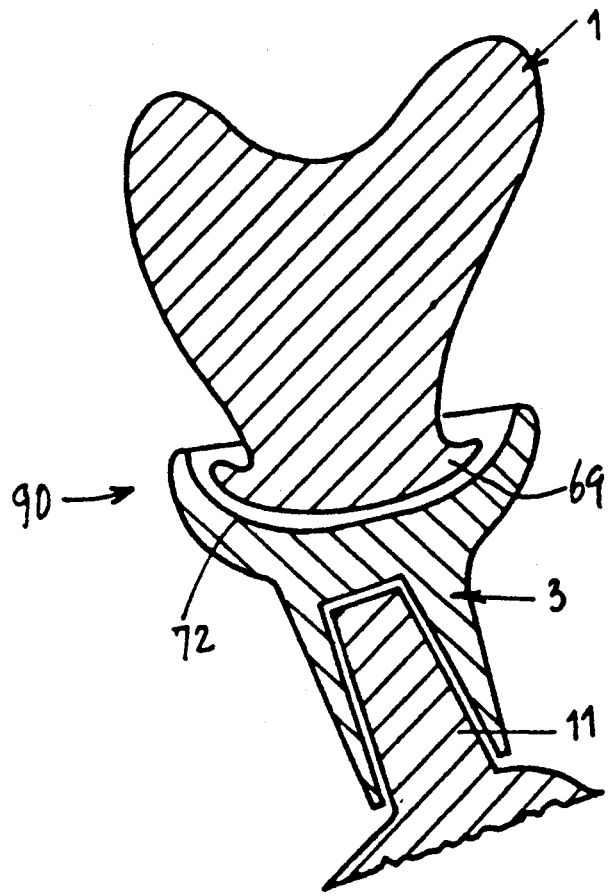
FIG. 18 is a fragmentary sectional view of a prosthesis which constitutes a modification of the prosthesis of FIG. 17.

FIG. 18 shows a somewhat modified universal joint 90 wherein the male coupling member or portion 69 extends into a relatively shallow pan-shaped socket 72. The male coupling member 69 of FIG. 17 or 18 can be carried by the adapter 3 and then extends into a complementary socket 72 in the head 1.

Figure 19:
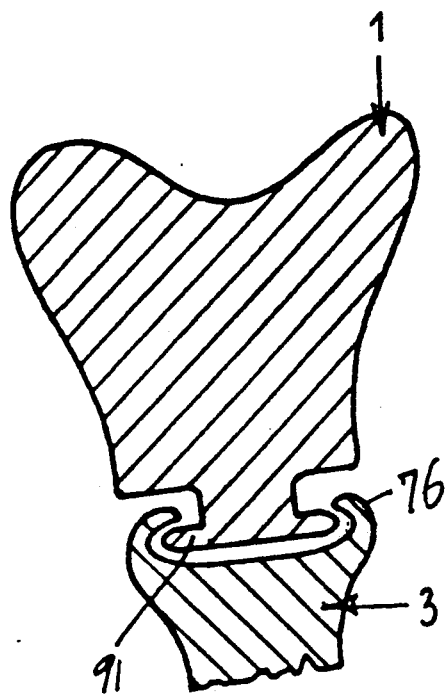
FIG. 19 is a fragmentary sectional view of a prosthesis wherein the coupling between the head and the adapter comprises a slide and a rail defining a track for the slide.

Referring to FIG. 19, there is shown a coupling with a slide 91 at the lower end of the head 1 and a rail 76 which is provided at the adjacent end of the adapter 3 and defines a track for the slide 91. The slide 91 and the rail 76 cooperate to hold the adapter 3 and the head 1 against movement away from each other. Such parts can be provided in addition to the universal joint of FIG. 17 or 18. Their purpose is to ensure that the implanted prosthesis remains properly assembled even if the muscles in the hip region of the patient are greatly damaged or weakened. If the damage to the muscles is very pronounced, the joint 90 of FIG. 17 or 18 does not suffice to ensure proper retention of the adapter 3 and head 1 in optimum positions relative to each other. The rail 76 preferably includes two halves which are mirror symmetrical to each other with reference to a plane extending at right angles to the plane of FIG. 19 and including the axis 30 of the head 1.

Figure 20:
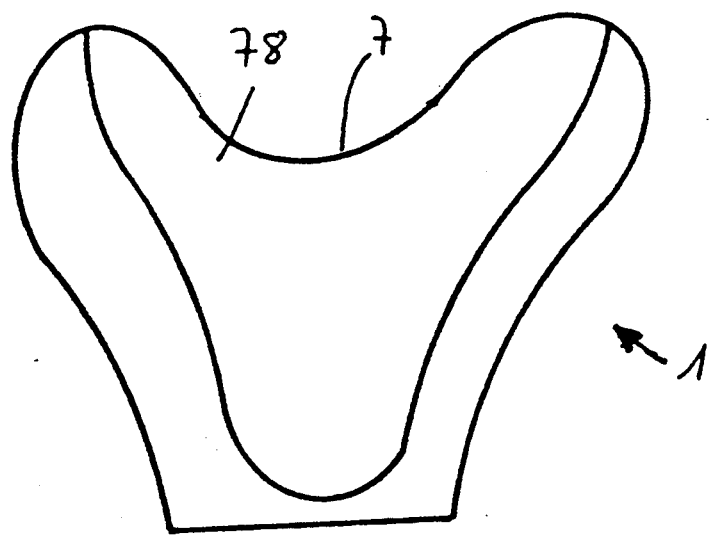
FIG. 20 is an elevational view of a head which is provided with a saddle-like layer of ceramic or other suitable material.

FIG. 20 shows that the seat 7 of the head 1 can be lined with a saddle-shaped layer 78 which can be made of or which can contain a suitable ceramic material. The purpose of the layer 78 is to reduce friction between the head 1 and the pelvic bone 6.

Figure 21:
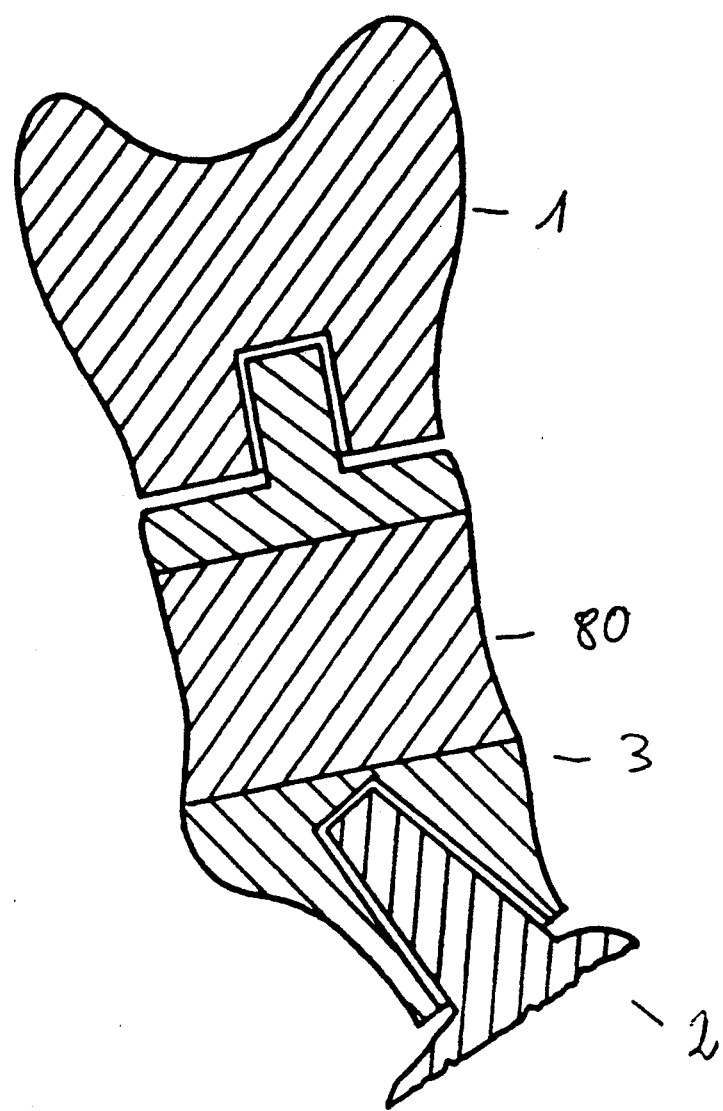
FIG. 21 is a fragmentary sectional view of a hip prosthesis with a damper installed in the adapter between the head and the shank.

The adapter 3 of FIG. 21 has a central portion 80 which constitutes a damper serving to absorb shocks when the wearer of the prosthesis is walking, running or jumping. The damper 80 can be made of a plastic which contains silicone.

FIG. 15 shows that the axis of the stub 34 forming part of the coupling between the adapter 3 and the shank 2 can be strongly inclined with reference to the axis of the shank 2 as well as with reference to the axis 30 of the head 1 and shaft 11.

The surgeon in charge of implantation of the improved hip prosthesis first removes the damaged or broken parts of the pelvic bone 6, and the shank 2 is embedded in the cavity 47 of the femur 40. The surgeon also finishes the surface bounding the recess 8 or opening of the pelvic bone 6 so that it conforms to the outline of the saddle-shaped surface bounding the seat 7 of the head 1. The head 1 is then assembled with the pelvic bone 6 and, if necessary, the surgeon inserts one or more distancing elements 15 between the head 1 and the adapter 3. It is also possible to insert one or more distancing elements between the adapter 3 and the shank 2 in addition to or in lieu of one or more distancing elements 15 between the head 1 and the adapter 3. Alternatively, the surgeon simply selects an adapter 3 of requisite length so that the implantation need not involve the utilization of one or more distancing elements.

If the prosthesis is of the type shown in FIG. 3, the adapter 3 is coupled to the head 1 by means of the shaft 11 (one or more distancing elements 15 can be placed between the lowermost portion 13 of the head 1 and the upper end portion of the adapter 3) and the shaft 11 is then secured in the hole 12 of the adapter 3 by means of the fastener 21. The insert 37 holds the adapter 3 against undesirable rotation relative to the shank 2 and/or vice versa.

When the implanting operation is completed, the muscles which orient the femur 40 engage in part the adapter 3 in the region of the portion 31 of line 29 and act upon the femur 40 with a large lever arm. As the healing of wounds progresses so that the patient is permitted to move the femur 40 relative to the pelvic bone 6, the forces acting upon the prosthesis turn the head 1 relative to the adapter 3 to thus relieve the surface bounding the recess 8 or the hole in the pelvic bone 6 of excessive stresses. The head 1 is normally stationary or nearly stationary relative to the pelvic bone 6 and is in large surface-to-surface contact with the latter. Due to the establishment of the relatively large lever arm as a result of engagement of muscles with the adapter 3 in the region of the portion 31 of line 29, the patient can contract her or his muscles to thereby influence the walking so as to at least resemble the walk of a person without an artificial hip joint.

The just discussed influence of the muscles which are attached to the femur 40 and act upon the adapter 3 at 31 is attributable, at least in part, to the aforementioned orientation of the axis 30 of . the head 1 as per force diagram of FIG. 15 and to the feature that the axis 32 of the shank 2 is laterally offset relative to the axis 30 of the head 1. Therefore, the patient can properly balance her or his body even if the center of gravity of the body is not always located exactly above the femur 40 while walking. On the contrary, the patient can shift the center of gravity of her or his body in the same way as a person without an artificial hip joint.

An advantage of the coupling between the head 1 and the adapter 3 is that the femur 40 can turn relative to the head 1 while the latter remains substantially stationary relative to the pelvic bone 6. This is advisable and desirable on several grounds. Thus, the horns 4, 5 of the head 1 need not repeatedly strike against the adjacent portions 9, 10 of the pelvic bone 6 when the patient is in motion. In addition, the head 1 can be relatively wide to establish a large surface-to-surface contact with the pelvic bone 6 and thus reduce the magnitude of stresses (i.e., to prevent the development of excessive localized stresses which could result in damage to and in further destruction of the pelvic bone). This can be accomplished without adversely influencing the ability of the patient to walk and the condition of the pelvic bone does not deteriorate as a result of excessive stressing.

The provision of a coupling between the head 1 and the adapter 3 is desirable and advantageous on the additional ground that the surgeon in charge of implantation can properly select the distance between the flange 41 of the shank 2 and the seat 7 of the head 1 in the course of the implanting operation because the shaft 11 can take one or more distancing elements 15. It is quite difficult or plain impossible to accurately ascertain the required or optimum distance between the flange 41 and the seat 7 prior to start of the implanting operation. The reason for the inability of even a highly experienced surgeon to accurately ascertain the required or optimum distance between the seat 7 and the flange 41 is that the extent of damage or injury to the pelvic bone 6 and/or to the femur 40 can only be determined with a requisite degree of accuracy only upon exposure of these bones in the course of the implanting operation. Each distancing element 15 can resemble a split ring with a central opening 17 and a slot extending from such central opening to the periphery so as to allow lateral insertion of one or more distancing elements in a manner as shown in FIG. 7. Alternatively, and as also shown in FIG. 7, the upper end of the shaft 11 can be retracted into the hole 12 of the adapter 3 so that one or more ring-shaped distancing elements 15 can be slipped sideways between the head 1 and the adapter 3 before the shaft 11 is lifted into the hole 14 of the head 1, e.g., by resorting to the tool 64 of FIG. 9. The tip of the tool 64 can be inserted into a socket 63 in the lower end face of the shaft 11. Proper selection of the distance between the seat 7 of the head 1 and the femur 40 when the prosthesis is implanted is important because this greatly reduces the danger of luxation of parts of the prosthesis relative to each other and relative to the bones.

The likelihood of luxation is further reduced by properly selecting the shape of the adapter 3 so as to ensure that it can be properly engaged by the adjacent muscles which influence the movements of the femur 40 relative to the pelvic bone 6 and the ability of the patient to walk without a pronounced limp, i.e., in a manner resembling the walk of a person with natural hip joints. Thus, the configuration of the adapter 3 will be selected by full consideration of the force diagram of FIG. 15. This renders it possible to dispense with distancing elements which is desirable for obvious reasons. Thus, the stability of the implanted prosthesis is enhanced if the number of implanted parts is kept to a minimum.

The lower end portion of the shank 2 can be mechanically secured to the adjacent portion of the femur 40 if the shank 2 is relatively long or very long. The mechanical fastening means can be of any suitable design (note the members 57 in FIG. 11).

The fastener 53 of FIG. 6 can be replaced with a wedge-like or with an otherwise configurated fastener.

When the implantation of the prosthesis is completed and the patient is capable of walking again, the muscles which are attached to the shank 2 pull the shank toward the head 1. This is due to the fact that such muscles are also attached to the pelvic bone 6. The resulting forces act upon the head 1 by way of the surface bounding the recess 8 of the pelvic bone 6 and upon the shank 2 by pulling the femur 40 toward the pelvic bone. The axes 30, 32 of the head 1 and shank 2 cross each other in an ordinary hip prosthesis. As described above, the axis 30 of the head 1 in the improved prosthesis is laterally offset with reference to and is substantially or exactly parallel with the axis 32 of the shank 2. In accordance with a presently preferred embodiment of the improved prosthesis, the axis 30 is substantially normal to a line extending between the tips of the horns 4, 5. The axis 30 and the line between the tips of the horns 4, 5 are located in a plane which further includes the lowermost center point of the head 1, and the axis 32 of the shank 2 is laterally offset relative to the axis 30 and may be located in the just mentioned plane and can be at least substantially parallel to the axis 30.

Referring again to FIG. 15, the resultant 68 is parallel to and preferably coincides with the axis 30. As explained above, the axis 30 is or can be substantially or exactly normal to a line which connects the tips of the horns 4 and 5, and such line and the axis 30 are preferably located in a common plane. This is particularly desirable if the adapter 3 and the head 1 are coupled to each other by a universal joint 90, i.e., the forces acting in the direction of the resultant 68 can be transmitted from the head 1 into the adapter 3 without strongly opposing (or without appreciably opposing) universal movements of the adapter 3 and head 1 relative to each other.

As already mentioned above, the configuration of the adapter 3 can be altered in a number of ways. Thus, it is not necessary that the entire adapter 3 exhibit an arcuate shape, i.e., it is possible to employ an adapter which includes one or more straight sections and one or more arcuate sections. For example, and in contrast to the adapter 3 of FIG. 3, the end portions of the adapter can be curved and its median portion can be substantially straight. The length of the substantially straight median portion or section of the adapter 3 will influence the realizable angle between a central axis of the straight median section and the axis 32 of the shank 2. The reason is that the adapter 3 acts not unlike a lever which stresses the shank 2 when the prosthesis is implanted. If the median section of the adapter 3 is relatively long, the inclination of such median section relative to the axis 32 is preferably rather small in order to avoid the transmission of excessive bending stresses to the shank 2 and femur 40.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contribution to the art and, therefore, such adaptations should and are intended to be comprehended within the meaning and range of equivalence of the appended claims.

We claim:

1. An implantable hip prosthesis for use between a pelvic bone which has an opening or a recess at its underside and a femur which has an upper end with a downwardly extending cavity, comprising a saddle-like head having two horns and a seat between the horns, said head being engageable with the pelvic bone so that the opening or the recess of the pelvic bone is adjacent the seat and is flanked by the horns of the head, and said head having surfaces which permit movement relative to the pelvic bone about a first predetermined axis which extends transverse to said seat and about a second predetermined axis which is substantially normal to said first predetermined axis; a shank which is implantable into the cavity of the femur; and connecting means for connecting said head to said shank, said connecting means including coupling means defining a pivot axis which substantially coincides with said first predetermined axis so as to permit turning of said head relative to said shank about said first predetermined axis.

2. The prosthesis of claim 1, said connecting means further comprising an adapter connecting said head with said shank.

3. The prosthesis of claim 2, wherein said adapter has a substantially S-shaped outline with a first end connected to said head and a second end connected to said shank.

4. The prosthesis of claim 3, wherein said first end has an upper end face which is inclined to the horizontal at an angle of 0–30 degrees in implanted condition of the prosthesis and in upright position of the patient wearing the prosthesis.

5. The prosthesis of claim 3, wherein said adapter has an underside which is adjacent said shank and is inclined with reference to the horizontal.

6. The prosthesis of claim 5, wherein said underside makes with the horizontal an angle of 0–60 degrees.

7. The prosthesis of claim 6, wherein said angle is approximately 30 degrees.

8. The prosthesis of claim 1, wherein said head has a wide convex surface bounding said seat and is adapted to engage the pelvic bone in the region of the recess or opening in implanted condition of the prosthesis.

9. The prosthesis of claim 1, said connecting means further comprising an adapter intermediate said head and said shank, and at least one distancing element intermediate said adapter and said head.

10. The prosthesis of claim 9, wherein said distancing element includes a disc.

11. The prosthesis of claim 10, wherein said disc has a hole with an axis which is substantially parallel with or substantially coincides with the axis of said head.

12. The prosthesis of claim 1, said connecting means further comprising an adapter intermediate said head and said shank, and coupling means being between said adapter and said head.

13. The prosthesis of claim 12, wherein said coupling means comprises a hole provided in said adapter and having an axis substantially coinciding with the first axis of said head, and a shaft extending from said head into said hole.

14. The prosthesis of claim 13, wherein said head has a blind hole for a portion of said shaft.

15. The prosthesis of claim 12, wherein said coupling means comprises a shaft having a portion extending into said adapter and means for non-rotatably securing said shaft to said adapter.

16. The prosthesis of claim 15, wherein said securing means comprises an externally threaded member and said adapter has a tapped hole for said externally threaded member.

17. The prosthesis of claim 16, wherein said threaded member has a tip which engages said shaft.

18. The prosthesis of claim 16, wherein said tapped hole is substantially horizontal in implanted condition of the prosthesis and in upright position of the person wearing the prosthesis.

19. The prosthesis of claim 12, wherein said coupling means comprises a shaft which is rigid with said adapter.

20. The prosthesis of claim 12, wherein said coupling means comprises a shaft which is rigid with said head and is rotatably mounted in said adapter.

21. The prosthesis of claim 12, said connecting means further comprising at least one distancing element between said adapter and said head, said coupling means comprising a shaft which is rigid with said distancing element.

22. The prosthesis of claim 1, said connecting means further comprising an adapter between said head and said shank and at least one distancing element interposed between said adapter and said head, said distancing element having a thickness conforming to the orthopedic requirements of the patient.

23. The prosthesis of claim 1, said connecting means further comprising an adapter between said head and said shank and a plurality of distancing elements interposed between said adapter and said head.

24. The prosthesis of claim 1, said connecting means further comprising an adapter between said head and said shank and a friction reducing lining interposed between said adapter and said head.

25. The prosthesis of claim 1, said connecting means further comprising an adapter interposed between said head and said shank, said coupling means including a shaft extending into said adapter and a bearing sleeve disposed between said shaft and said adapter.

26. The prosthesis of claim 1, said connecting means further comprising an adapter between said shank and said head and a coupling between said adapter and said shank, said coupling comprising a stub provided on said shank and a socket provided in said adapter and receiving said stub.

27. The prosthesis of claim 26, wherein said stub has a substantially conical shape and tapers in a direction away from said shank.

28. The prosthesis of claim 26, wherein said shank has a common axis with said stub.

29. The prosthesis of claim 1, said connecting means further comprising an adapter between said shank and said head and a coupling between said adapter and said shank, said coupling comprising a stub provided on said adapter and a socket provided in said shank and receiving said stub.

30. The prosthesis of claim 1, said connecting means further comprising an adapter between said head and said shank and a coupling between said adapter and said shank, said coupling comprising a stub on one of the parts including said adapter and said shank, a socket provided in the other of said parts and receiving said stub, and means for non-rotatably holding said stub in said socket.

31. The prosthesis of claim 1, said connecting means further comprising an adapter between said head and said shank and a coupling between said shank and said adapter, said coupling including a substantially conical stub which tapers in a direction from said shank toward said adapter.

32. The prosthesis of claim 1, said connecting means further comprising an adapter between said head and said shank and a coupling between said shank and said adapter, said coupling comprising a substantially cylindrical stub provided on one of the parts including said shank and said adapter and a complementary socket provided in the other of said parts and receiving said stub.

33. The prosthesis of claim 32, wherein said shank and stub have offset axes.

34. The prosthesis of claim 1, said connecting means further comprising an adapter between said head and said shank and means for non-rotatably securing said adapter to said head.

35. The prosthesis of claim 1, further comprising means for securing the head to the pelvic bone or to another part of the anatomy of the patient wearing the prosthesis.

36. The prosthesis of claim 35, said connecting means further comprising an adapter between said head and said shank, said securing means being arranged to be connected to the pelvic bone of the patient wearing the prosthesis and to at least one of the parts including the head and the adapter.

37. The prosthesis of claim 35, further comprising means for promoting the growth of bones adjacent to the securing means.

38. The prosthesis of claim 37, wherein said promoting means comprises portions of bones.

39. The prosthesis of claim 35, wherein said securing means includes a portion of a bone.

40. The prosthesis of claim 1, said connecting means further comprising an adapter between said head and said shank, an externally toothed shaft provided on said adapter and a hole provided in said head and receiving said shaft, said head having internal teeth provided in said hole and mating with the external teeth of said shaft.

41. The prosthesis of claim 1, said connecting means further comprising an adapter between said head and said shank, a shaft provided on one of the parts including said adapter and said head, a hole provided in the other of said parts and receiving said shaft, and a threaded fastener extending through said shaft and securing said head to said adapter.

42. The prosthesis of claim 1, said connecting means further comprising an adapter between said head and said shank, said adapter having a first surface adjacent said head and said head having a second surface adjacent said first surface, said connecting means comprising teeth provided on one of said surfaces and tooth spaces provided for said teeth in the other of said surfaces.

43. The prosthesis of claim 1, said connecting means further comprising a flange which is disposed between said head and said shank and overlies the femur when the shank is implanted in the cavity of the femur.

44. The prosthesis of claim 1, wherein said shank has an external surface and at least the major portion of said external surface is smooth.

45. The prosthesis of claim 1, wherein said shank has at least one longitudinally extending flute.

46. The prosthesis of claim 45, wherein said shank has at least one sharp edge adjacent said flute.

47. The prosthesis of claim 1, wherein said shank is arranged to be a tight fit in the cavity of the femur so that it can be implanted without the need for introduction of bone cement therearound.

48. The prosthesis of claim 1, wherein said shank is elongated and has an end portion remote from said head; and further comprising means for connecting said end portion to the femur of the patient wearing the prosthesis.

49. The prosthesis of claim 1, further comprising bone material inserted into the cavity of the femur into which the shank is implanted, said shank having an end portion adjacent said head and said bone material surrounding said end portion of the shank.

50. The prosthesis of claim 1, further comprising bone cement surrounding at least a portion of the implanted shank.

51. The prosthesis of claim 1, wherein said shank constitutes a total femoral prosthesis.

52. The prosthesis of claim 1, wherein said shank includes a female section and a male section extending into said female section.

53. The prosthesis of claim 52, wherein said female section is disposed between said head and said male section and a portion of said male section extends from said female section in a direction away from said head.

54. The prosthesis of claim 52, wherein said female section includes a Reimers lock.

55. The prosthesis of claim 52, further comprising means for securing said male section to said female section.

56. The prosthesis of claim 55, wherein said securing means comprises a threaded fastener.

57. The prosthesis of claim 55, wherein said securing means comprises a pin.

58. The prosthesis of claim 1, wherein at least a portion of said head consists of a metallic material.

59. The prosthesis of claim 58, wherein said metallic material includes titanium.

60. The prosthesis of claim 1, wherein at least a portion of said head consists of a plastic material.

61. The prosthesis of claim 1, wherein at least a portion of said head consists of a ceramic material.

62. The prosthesis of claim 1, further comprising a friction reducing layer provided at least on that portion of said head which bounds said seat.

63. The prosthesis of claim 62, wherein said layer contains a ceramic material.

64. The prosthesis of claim 62, wherein said layer resembles a saddle.

65. The prosthesis of claim 1, said connecting means further comprising an adapter between said head and said shank, at least a portion of said adapter containing a metallic material.

66. The prosthesis of claim 65, wherein said metallic material is titanium.

67. The prosthesis of claim 1, said connecting means further comprising an adapter between said head and said shank, at least a portion of said adapter consisting of a plastic material.

68. The prosthesis of claim 1, said connecting means further comprising an adapter between said head and said shank, at least a portion of said adapter consisting of a ceramic material.

69. The prosthesis of claim 1, said connecting means further comprising an adapter between said head and said shank, said coupling means comprising a shaft provided on one of the parts including said adapter and said head, a hole provided in the other of said parts and receiving said shaft, and a friction reducing lining surrounding said hole, said lining containing a plastic material.

70. The prosthesis of claim 69, wherein said plastic material is polyethylene.

71. The prosthesis of claim 1, said connecting means further comprising an adapter between said head and said shank, said coupling means comprising a shaft anchored in one of the parts including said head and said adapter, a hole for said shaft in the other of said parts, and a plastic lining surrounding the shaft in at least one of said parts.

72. The prosthesis of claim 1, said connecting means further comprising a relatively large flange interposed between said head and said shank and arranged to overlie the femur whose cavity receives said shank.

73. The prosthesis of claim 1, said connecting means further comprising an adapter between said shank and said head, said coupling means comprising a shaft having a first portion extending into said head and a second portion extending into said adapter, said adapter having a hole which receives said second portion of said shaft and has an open end affording access to said shaft; and further comprising a tool arranged to engage the shaft by way of the open end of said hole.

74. The prosthesis of claim 1, wherein said head has an external surface including a portion bounding said seat and arranged to contact the pelvis when the prosthesis is implanted, said first predetermined axis intersecting said portion of said surface.

75. The prosthesis of claim 1, said connecting means further comprising an adapter between said shank and said head, said coupling means comprising a shaft provided on one of the parts including said head and said adapter and a hole provided in the other of said parts and receiving said shaft, said shaft having an axis which is parallel with or coincides with the resultant of the weight acting upon the head in implanted condition of the prosthesis and a force representing the action of muscles upon the implanted prosthesis.

76. The prosthesis of claim 75, wherein the axis of said shaft makes with the vertical an angle of 0–30 degrees in upright position of the person wearing the prosthesis.

77. The prosthesis of claim 76, wherein said angle is approximately 16 degrees.

78. The prosthesis of claim 1, said connecting means further comprising an adapter between said head and said shank, said adapter having a surface facing said head and said coupling means comprising a shaft projecting from said surface and extending into a hole provided therefor in said head.

79. The prosthesis of claim 1, said connecting means comprising a universal joint.

80. The prosthesis of claim 79, wherein said universal joint includes a spherical portion and a complementary socket for said spherical portion.

81. The prosthesis of claim 79, wherein said universal joint includes a pan-shaped socket and a male component in said socket.

82. The prosthesis of claim 1, said connecting means further comprising an adapter between said head and said shank and a joint between said head and said adapter, said last named joint comprising a slide on one of the parts including said head and said adapter and a rail defining a track for said slide and provided on the other of said parts.

83. The prosthesis of claim 1, said connecting means further comprising an adapter between said head and said shank and damper means interposed between said adapter and said head.

84. The prosthesis of claim 1, said connecting means further comprising an adapter between said shank and said head, said adapter having a surface adjacent said head and said predetermined axis being substantially normal to said surface.

85. The prosthesis of claim 1, said connecting means further comprising a substantially S-shaped adapter between said head and said shank, said adapter having a substantially straight portion having a predetermined length and a predetermined inclination to the horizontal in upright position of the patient wearing the prosthesis, the ratio of said length to said inclination being a constant.

86. The prosthesis of claim 1, wherein said shank has, an additional axis which is laterally offset with reference to said first predetermined axis.

87. The prosthesis of claim 86, wherein first said predetermined axis substantially coincides with the resultant of a first force which is applied by the weight resting on the head and a second force which is applied to the head by muscles.

88. The prosthesis of claim 1, wherein said connecting means is designed to releasably connect said head to said shank.

* * * * *